US00PP20794P3

(12) United States Plant Patent
Chuawong

(10) Patent No.: US PP20,794 P3
(45) Date of Patent: Mar. 2, 2010

(54) ***DIANELLA CAERULEA* PLANT NAMED 'JOHN 316'**

(50) Latin Name: *Dianella caerulea*
Varietal Denomination: John 316

(76) Inventor: Nuanong Chuawong, 817 Castlereagh Road, Castlereagh, NSW, 2749 (AU)

( * ) Notice: Subject to any disclaimer, the term of this patent is extended or adjusted under 35 U.S.C. 154(b) by 0 days.

(21) Appl. No.: 12/070,119

(22) Filed: Feb. 15, 2008

(65) Prior Publication Data

US 2009/0210986 P1 Aug. 20, 2009

(51) Int. Cl.
*A01H 5/00* (2006.01)

(52) U.S. Cl. ..... Plt./424

(58) Field of Classification Search ..... Plt./424
See application file for complete search history.

*Primary Examiner*—Susan B McCormick Ewoldt

(57) ABSTRACT

'John 316' is a distinctive variety of *Dianella caerulea*, which is characterized by the combination of its tall plant height, an absence of canes, strong leaf surface glaucosity creating a blue-green foliage appearance, violet blue flowers, long inflorescence length positioning the flowers above the foliage and a red basal sheath zone. 'John 316' is also less prone to falling over than the parent type.

5 Drawing Sheets

Latin name of the genus and species: The Latin name of the novel variety disclosed herein is *Dianella caerulea*.

Variety denomination: The inventive variety of *Dianella caerulea* disclosed herein has been given the varietal denomination 'John 316'.

BACKGROUND OF THE INVENTION

The present invention relates to a new and distinct perennial Blue Flax Lily variety of *Dianella caerulea*, which has been given the varietal denomination of 'John 316'. The market class for 'John 316' is that of an ornamental grass-like plant. 'John 316' is intended for use in landscaping and as a decorative grass-like plant.

An application for Plant Breeders' Rights for variety 'John 316' has been filed with the Australian Plant Breeders' Rights Office, and was first gazetted in the Australian Plant Breeders' Rights database in March 2006 under Application No. 2006/035.

Parentage: The *Dianella caerulea* variety 'John 316' was first discovered in 2002 in an Australian nursery in Castlereagh, New South Wales as a seedling selection derived from open pollinated seedlings of *Dianella caerulea* 'Sydney Ecotype' which was selected due to differences in growth habit and colour compared to the parent plant. The parent plant, 'Sydney Ecotype' (unpatented), is characterized by its tall plant height, a medium plant density, medium length aerial stems, a yellow-green leaf colour and flowers positioned typically within the foliage.

In 1999, *Dianella caerulea* collected from the Sydney area ('Sydney Ecotype'), were grown together in an open bed covering approximately 250 square meters of area. The plants were allowed to develop seed by open pollination.

Approximately 10000 seed were collected in September 1999 and grown on during 2000 During 2001–2002 two plant were identified as having a glaucous leaf surface texture creating an overall bluish green leaf color. They were selected and grown further for evaluation. Finally in 2004 a single plant from these was selected as having desirable traits using the selection criteria of bluish leaf color (strong leaf glaucosity), tall plant height, a red basal sheath zone and blue flowers.

This plant was subsequently initiated into micropropagation for further vegetative multiplication.

Asexual reproduction. 'John 316' was first asexually propagated by vegetative division in 2003 in the state of New South Wales, Australia. 'John 316' was asexually reproduced again during 2004 and 2005 and confirmed to be stable in character. The distinctive characteristics of the inventive variety, 'John 316', have remained stable and true to type from generation to generation through successive cycles of asexual reproduction including vegetative division and micropropagation.

SUMMARY OF THE INVENTION

'John 316' is a distinctive variety of *Dianella caerulea*, which is characterized by the combination of its tall plant height, an absence of canes, strong leaf surface glaucosity creating a blue-green foliage appearance, violet blue flowers, long inflorescence length positioning the flowers above the foliage and a red basal sheath zone. 'John 316' is also less prone to falling over than the parent type.

BRIEF DESCRIPTION OF THE FIGURES

The photographs in the drawings were made using conventional techniques and show the colours as true as reasonably possible by conventional photography. Colours in the photographs may differ slightly from the colour values cited in the detailed botanical description, which accurately describe the colours of the new *Dianella caerulea*.

FIG. 3 shows a 12 month old 'John 316' plant flower illustrating the violet blue color of the petals, yellow orange anther color and petal reflexing.

BOTANICAL DESCRIPTION OF THE PLANT

The following is a detailed botanical description of a new and distinct variety of a *Dianella caerulea* ornamental grass-like plant known as 'John 316'. The descriptions disclosed herein are based upon observations of the plant grown in 200 mm nursery pots and field plots in New South Wales, Australia. The plants were approximately 12-months-old at the time of observation. All colours cited herein refer to The Royal Horticultural Society Colour Chart (The Royal Horticultural Society, London, 1995 edition).

Those skilled in the art will appreciate that certain characteristics will vary with older or, conversely, younger plants. 'John 316' has not been observed under all possible environmental conditions. Where dimensions, sizes, colours and other characteristics are given, it is to be understood that such characteristics are approximations or averages set forth as accurately as practicable. The phenotype of the variety may differ with variations in the environment such as season, temperature, light intensity, day length, cultural conditions and the like.

Figure 1:
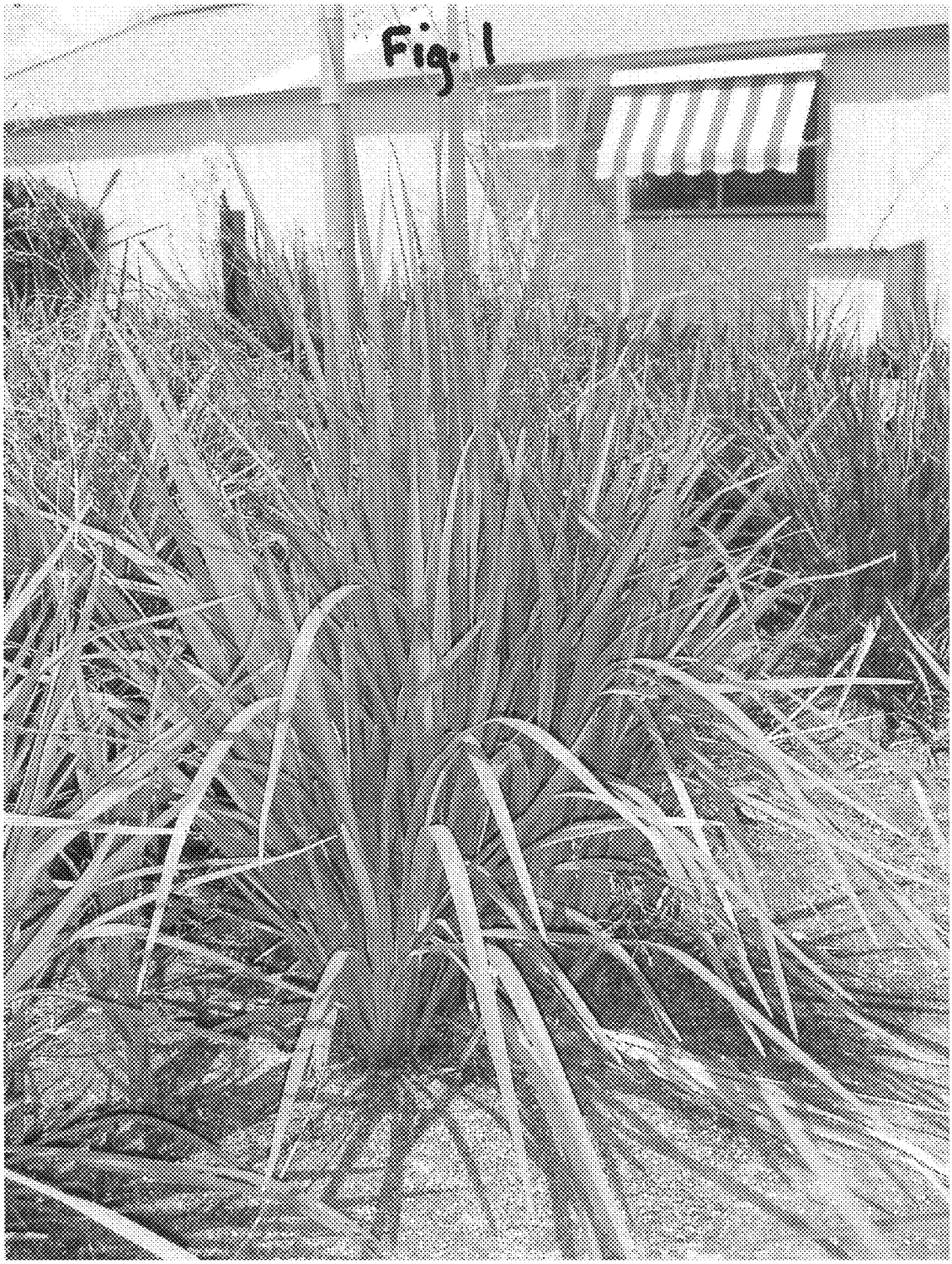
FIG. 1 shows a 12 month old 'John 316' plant and illustrates the absence of canes and tall plant and flower height, strong leaf glaucosity and red basal sheath zone as compared with other *Dianella caerulea*.
Figure 2:
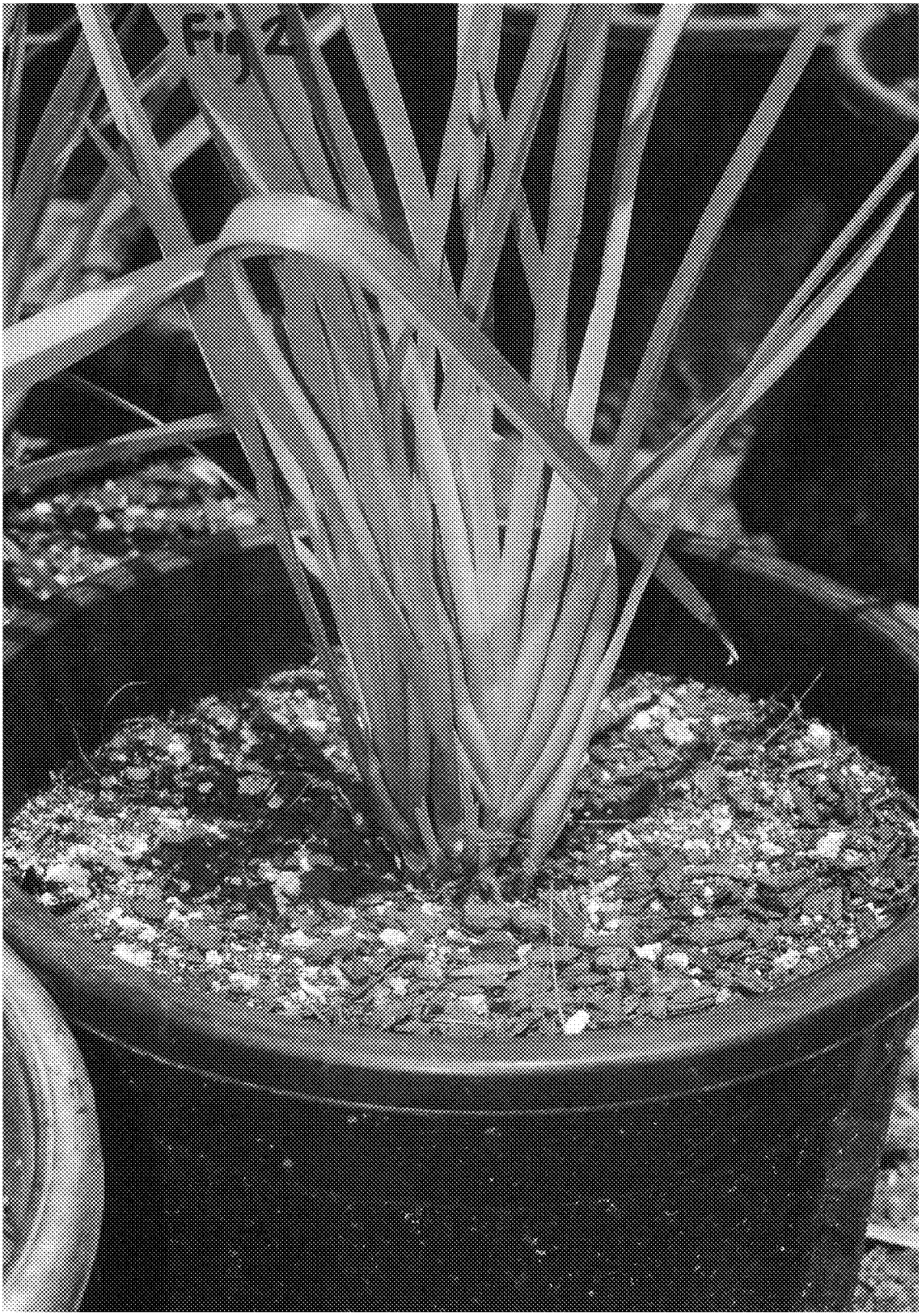
FIG. 2 shows a red basal sheath zone of a 16 week old 'John 316' plant and also illustrates the absence of canes as compared with other *Dianella caerulea*.
Figure 5:
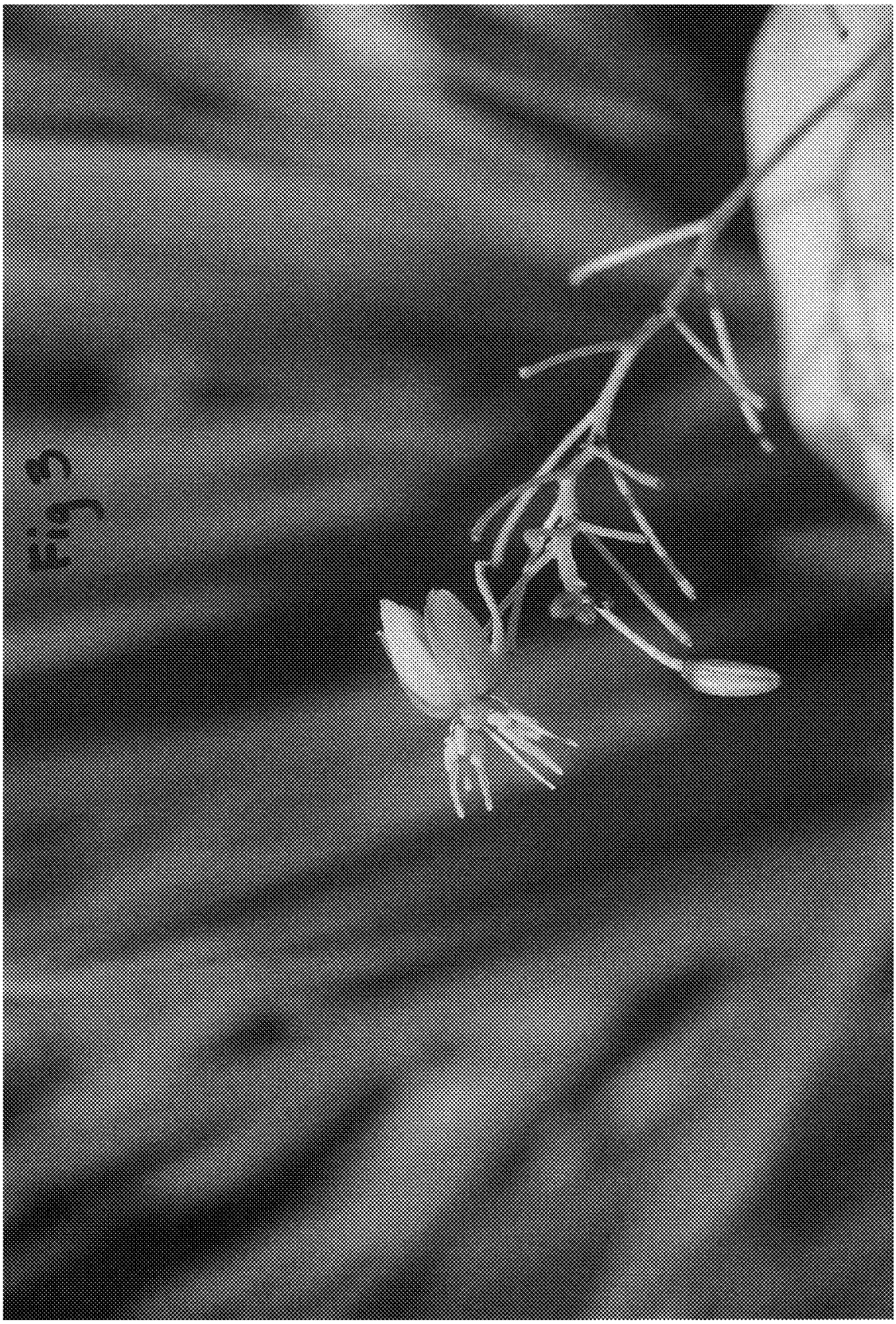
FIG. 5 shows ripened berries of a 12 month old 'John 316' plant showing violet blue coloration.
Figure 4:
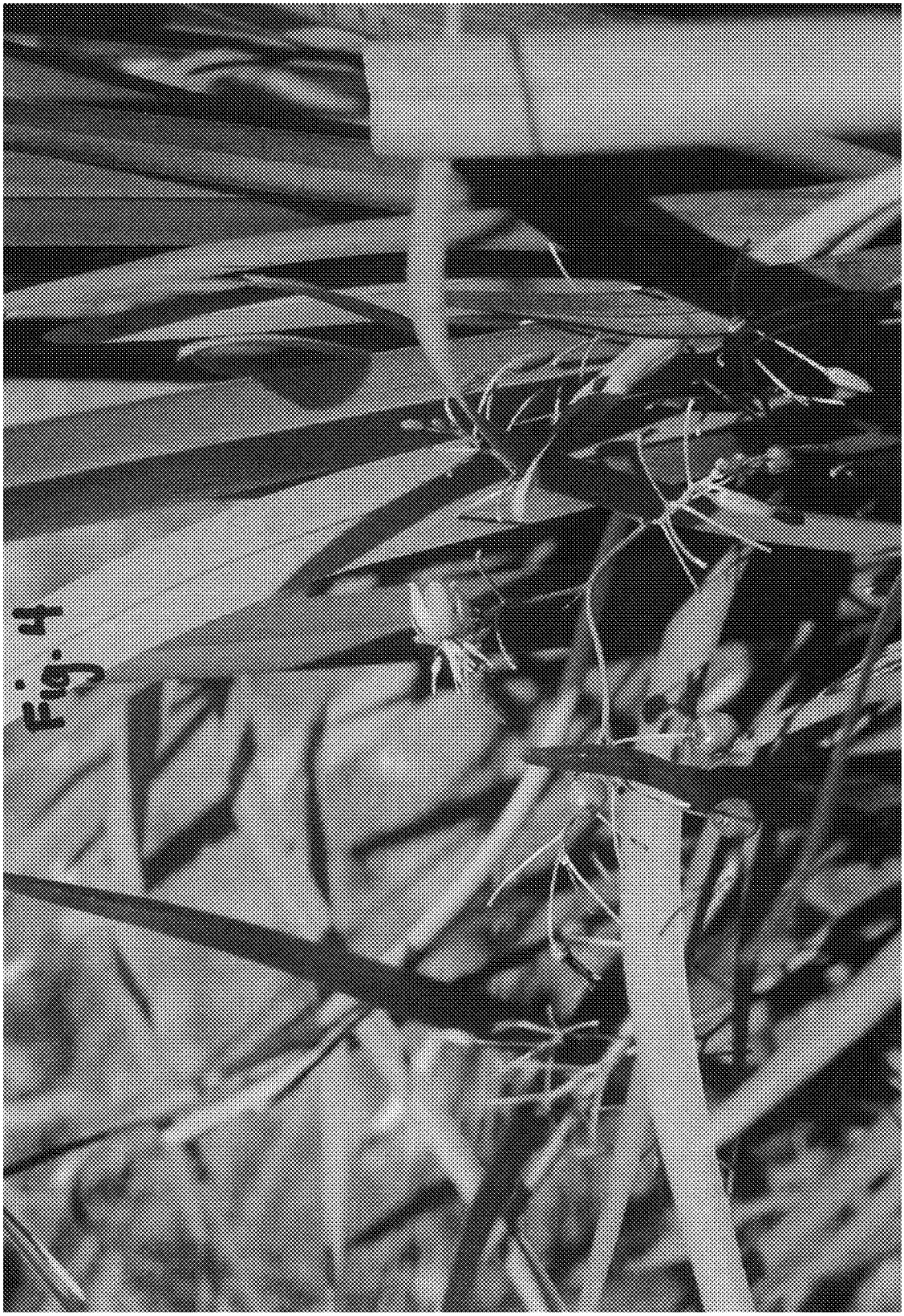
FIG. 4 shows un-ripened berries of a 12 month old 'John 316' plant showing green coloration.

'John 316' is a perennial *Dianella caerulea* plant, which was produced through an innovative breeding program. After its selection, 'John 316' was asexually propagated by division and micropropagation. 'John 316' has dense growth, slightly spreading and a semi-compact growth habit, a short rhizome form, no canes, a blue-green foliage colour, a violet blue flower colour, and a reduced tendency to fall over at maturity. A botanical description of 'John 316' and a comparison with other varieties of *Dianella caerulea* are provided below. A representative *Dianella caerulea* 'John 316' plant is shown in FIG. 1.

Technical description of the variety:

*Growth habit.*—'John 316' is a tall, rhizomatous plant with an absence of canes forming a semi-compact tussock. Its growth habit is erect, its height is tall (70–80 cm foliage, 90–110 cm inflorescence), width is medium (range 60–70 cm) and the density of its shoots is strong.

*Stem.*—Length of internodes is short compared to the parent form with an internode length ranging 3 mm to 5 mm.

*Foliage.*—Leaf attitude is erect to semi-erect, leaf length long (70–80 mm), leaf width medium (13–14 mm), upper side colour with waxiness removed yellow-green (RHS 146A), upper side colour with waxiness retained greyed-green (RHS 189A), lower side color with waxiness removed yellow-green (RHS 147B), upper side glaucosity strong, shape ligulate, apex acute, cross section concave, margin entire. Average number of leaves per 12 month old plant is approximately 120.

*Basal sheath.*—Appearance is reddish, denoted approximately by RHS reference grayed orange (RHS 175A).

*Inflorescence.*—The inflorescence (flower spike) is tall (length range 90–110 cm), position of flowers is above the foliage, number of leaves per inflorescence on a 12 month old plant is approximately 130. Peduncle color is yellow green (RHS 146A).

*Flowers.*—Flower color (upper and lower side of petals) is violet blue corresponding to RHS 94B–C. Flower diameter is medium (range 9–12 mm) and anthers are yellow orange corresponding to RHS 23A. Tepal number is six, tepals are reflexed, tepal shape is elliptic, tepal margin is entire, tepal length is 8–11 mm, tepal width is 2—3 mm. Bud length is medium (range 8–11 mm), bud diameter is medium (range 2.5–3.5 mm). Bud shape is elliptic. Bud color is a dark bluish appearance created by a combination of violet blue (approximately RHS 89A) tepal formation in close contact with junction of petiole colored yellow green (146A–B). Petiole length range is 10–15 mm.

Anther color is yellow (approximately RHS 6A) to yellow orange (approximately RHS 14A). Filament color is violet blue RHS 94B–C. Stamen length is approximately 7–8 mm. Stigma length is 8–12 mm, stigma color approximately violet blue RHS 91D.

*Fruit.*—A succulent berry, length to 11 mm, shape is globose, sometimes asymmetrical, color of unripe berry is yellow green (RHS 146A) and color of ripe berry is approximately violet blue (RHS 89A), surface texture is smooth and glossy. Seed color is black (RHS 202A), seed number per berry 1 to 3, seed length is approximately 5 to 7 mm.

*Environmental tolerances.*—'John 316' has shown potential for shade tolerance. The winter hardiness of 'John 316' is at least to −12 degrees Celsius. 'John 316' has been observed to hold colour to −8 degrees Celsius. 'John 316' has good colour retention in winter and normal drought tolerance, compared to the common form of this plant. 'John 316' has also shown potential for tolerance to periodical wetting from rain or irrigation for several days.

*Disease resistance and susceptibility.*—'John 316' has excellent tolerance to pests and diseases and good resistance to root rot, which is a common problem in *Dianella caerulea.*

These features and other characteristics of the plant are apparent from the figures.

'John 316' Compared to Other Varieties of *Dianella caerulea*

Grouping characteristics used to identify the most similar varieties of common knowledge to 'John 316' included tall plant height, strong leaf surface glaucosity, short canes and dense growth habit. Based on this, 'DBB03' (U.S. Plant Pat. No. 17,998 filed Sep. 29, 2005; Australian Plant Breeders Rights Application No. 2003/291), and DCNCO (U.S. Plant Pat. No. 18,505 filed Sep. 29, 2005 Australian Plant Breeders Rights Application No. 2003/293) are considered to be the most similar varieties. No other similar varieties were identified.

In comparing 'John 316' with the growth habit of the parent form of *Dianella caerulea* 'Sydney ecotype' 'John 316' has a more dense growth habit than 'Sydney Ecotype'. 'John 316' has an absence of aerial stems (canes) whereas the 'Sydney Ecotype' has medium to long canes. 'John 316' has a long inflorescence positioned above the foliage whereas the 'Sydney Ecotype' has medium inflorescence length positioned within the foliage. The surface texture of the leaf of 'John 316' has a strong glaucosity whereas the 'Sydney Ecotype' has a weak glaucosity.

In comparing 'John 316' with other *Dianella caerulea* varieties, 'John 316' has a tall plant height whereas 'DBB03' is short. 'John 316' has a reddish colored basal sheath zone whereas 'DBB03' is green. 'John 316' has a long inflorescence length whereas 'DBB03' is short. 'John 316' has a leaf surface texture with strong glaucosity (foliage appearance is blue green) whereas 'DCNCO' is weak (foliage appearance is green). 'John 316' has a long inflorescence positioned above the foliage whereas the 'DCNCO' has medium inflorescence length positioned within the foliage.

That which is claimed is:

1. A new and distinct variety of *Dianella caerulea* plant named 'John 316', substantially as described and illustrated herein.

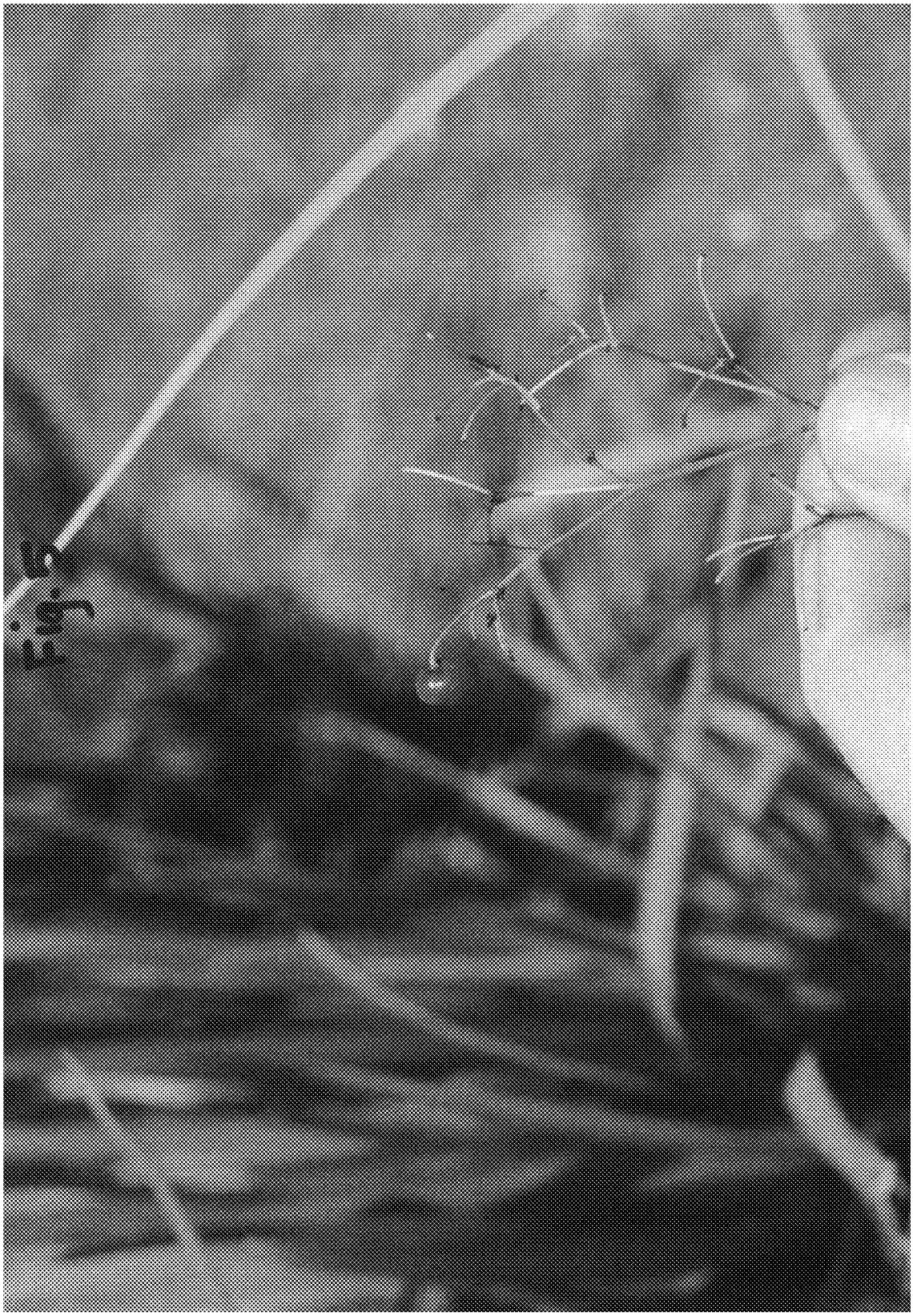

* * * * *